United States Patent
Borgia et al.

(10) Patent No.: US 10,365,281 B2
(45) Date of Patent: Jul. 30, 2019

(54) BIOMARKERS OF RAPID PROGRESSION IN ADVANCED NON-SMALL CELL LUNG CANCER

(71) Applicant: Rush University Medical Center, Chicago, IL (US)

(72) Inventors: Jeffrey A. Borgia, Chicago, IL (US); Sanjib Basu, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 218 days.

(21) Appl. No.: 15/102,647

(22) PCT Filed: Dec. 8, 2014

(86) PCT No.: PCT/US2014/069009
§ 371 (c)(1),
(2) Date: Jun. 8, 2016

(87) PCT Pub. No.: WO2015/088947
PCT Pub. Date: Jun. 18, 2015

(65) Prior Publication Data
US 2016/0313336 A1    Oct. 27, 2016

Related U.S. Application Data

(60) Provisional application No. 61/913,740, filed on Dec. 9, 2013.

(51) Int. Cl.
*G01N 33/53* (2006.01)
*G01N 33/574* (2006.01)

(52) U.S. Cl.
CPC .............................. *G01N 33/57423* (2013.01)

(58) Field of Classification Search
None
See application file for complete search history.

(56) References Cited

U.S. PATENT DOCUMENTS

| | | |
|---|---|---|
| 2003/0219768 A1 | 11/2003 | Beebe |
| 2003/0224509 A1 | 12/2003 | Moon et al. |
| 2004/0091857 A1 | 5/2004 | Nallur |
| 2008/0160546 A1 | 7/2008 | Colpitts et al. |
| 2009/0047689 A1 | 2/2009 | Kolman |
| 2009/0176228 A1 | 7/2009 | Birse et al. |
| 2009/0233268 A1 | 9/2009 | Lin et al. |
| 2010/0009386 A1 | 1/2010 | Streeper et al. |
| 2010/0119537 A1 | 5/2010 | Podack |
| 2010/0152058 A1 | 6/2010 | Di Fiore et al. |
| 2010/0176228 A1 | 7/2010 | Huang |
| 2010/0240081 A1 | 9/2010 | Rollinger et al. |
| 2011/0318336 A1 | 12/2011 | Petricoin, III et al. |
| 2012/0094863 A1 | 4/2012 | Stroh |
| 2012/0115745 A1 | 5/2012 | McKeegan et al. |
| 2012/0178111 A1 | 7/2012 | Diamandis et al. |
| 2013/0225442 A1 | 8/2013 | Borgia |

FOREIGN PATENT DOCUMENTS

| | | |
|---|---|---|
| WO | WO 2003/000928 A2 | 1/2003 |
| WO | WO 2009/028580 A1 | 3/2009 |
| WO | WO 2009/067546 A2 | 5/2009 |
| WO | WO 2012/054732 A2 * | 4/2012 |

OTHER PUBLICATIONS

Orlova (Journal of Translational Medicine 2011 9:195).*
Niewczas et al (Clin J Am Soc Nephrol, 2009, 4: 62-70).*
Grunnet et al (Diabetologia, 2006, 49: 343-350).*
Slotwinski et al (Annals of Transplantation, 2002, 7(3):36-39).*
Jankowska, R. et al.; "Serum Antibodies to Retinal Antigens in Lung Cancer and Sarcoidosis"; Pathobiology, vol. 71, No. 6; Dec. 2004; pp. 323-328; Abstract.
Aberle DR et al.; "Reduced Lung-Cancer Mortality with Low-Dose Computed Tomographic Screening"; The New England Journal of Medicine, vol. 365, No. 5; Aug. 4, 2011; pp. 395-409.
American Cancer Society; "Cancer Facts & Figures 2013"; 2013 [cited 2013 Jun. 6, 2013]; 64 pages; Available from: http://www.cancer.org/acs/groups/content/@epidemiologysurveilance/documents/document/acspc-036845.adf.
Alemàn, M. et al.; "Leptin Role in Advanced Lung Cancer. A Mediator of the Acute Phase Response or a Marker of the Status of Nutrition?"; Cytokine, vol. 19, No. 1; Jul. 7, 2002; pp. 21-26.
Bach PB et al.; "Benefits and Harms of CT Screening for Lung Cancer: A Systematic Review"; JAMA, vol. 307, No. 22; Jun. 13, 2012; pp. 2418-2429.
Bach PB et al.; Screening for Lung Cancer: ACCP Evidence-Based Clinical Practice Guidelines (2nd edition); Chest; Sep. 2007 Supplement; pp. 69S-77S.
Bach PB et al.; "Computed Tomography Screening and Lung Cancer Outcomes"; JAMA, vol. 297, No. 9; Mar. 7, 2007; pp. 953-961.
Bigbee WL et al.; "A Multiplexed Serum Biomarker Immunoassay Panel Discriminates Clinical Lung Cancer Patients from High-Risk Individuals Found to Be Cancer-Free by CT Screening"; Journal of Thoracic Oncology, vol. 7, No. 4; Apr. 2012; pp. 698-708.
Borgia JA et al.; "Establishment of a Multi-Analyte Serum Biomarker Panel to Identify Lymph Node Metastases in Non-Small Cell Lung Cancer"; Journal of Thoracic Oncology, vol. 4, No. 3; Mar. 2009; pp. 338-347.

(Continued)

*Primary Examiner* — Sean E Aeder
(74) *Attorney, Agent, or Firm* — Brinks Gilson & Lione

(57) ABSTRACT

Methods and kits for identifying rapidly progressing lung cancer in a subject are provided. The method includes obtaining a biological sample from the subject and assaying a level of a biomarker in a biomarker panel in the biological sample where the panel includes at least one biomarker selected from Table I or Table II. The method further includes determining with the subject is treatment naive or has received at least one treatment; and comparing the level of the biomarker in the subject's sample to a cutoff value listed in Table I for treatment naive subjects or Table II for previously treated subjects. The method further includes determining whether the subject's level is above or below the cutoff value to determine whether the subject has rapidly progressing lung cancer.

5 Claims, 6 Drawing Sheets

(56) References Cited

OTHER PUBLICATIONS

Borgia JA et al.; "Prognostic Value of Circulating Angiogenesis Biomarkers in Rapidly Progressing NSCLC"; The joint AACR-IASLC meeting on the Molecular Origins of Lung Cancer, San Diego, CA; Jan. 6-9, 2014; one page.
Boyle P et al.; "Clinical validation of an autoantibody test for lung cancer"; Annals of Oncology; Dec. 2011; pp. 383-389.
Breiman L; "Random Forests"; Machine Learning, vol. 45, Issue 1; Oct. 2001; pp. 5-32.
Breiman L et al.; "Classification and Regression Trees"; 36-350, Data Mining; Nov. 6, 2009; 25 pages.
Brichory, F. et al.; "An immune response manifested by the common occurrence of annexins I and II autoantibodies and high circulating levels of IL-6 in lung cancer"; Proceedings of the National Academy of Sciences of the United States of America, vol. 98, No. 17; Aug. 14, 2001; 9824-9.
Buccheri G et al.; "Clinical Equivalence of Two Cytokeratin Markers in Non-Small Cell Lung Cancer: A Study of Tissue Polypeptide Antigen and Cytokeratin 19 Fragments"; Chest; Aug. 2003; pp. 622-632.
Carpagnano, G. et al.; "IL-2, TNF-α, and Leptin: Local Versus Systemic Concentrations in NSCLC Patients"; Oncology Research, vol. 16; Aug. 2007; pp. 375-381.
Farlow EC et al.; "A multi-analyte serum test for the detection of non-small cell lung cancer"; British Journal of Cancer; Sep. 21, 2010; pp. 1221-1228.
Farlow EC et al.; "Development of a Multiplexed Tumor-Associated Autoantibody-Based Blood Test for the Detection of Non-Small Cell Lung Cancer"; Clin Cancer Res; Jul. 1, 2010; pp. 3452-3462.
Fidias PM et al.; "Phase III study of immediate compared with delayed docetaxel after front-line therapy with gemcitabine plus carboplatin in advanced non-small-cell lung cancer"; J Clin Oncol, vol. 27; Feb. 1, 2009; pp. 591-598.
Field JK et al.; "International Association for the Study of Lung Cancer Computed Tomography Screening Workshop 2011 Report"; Journal of Thoracic Oncology, vol. 7, No. 1; Jan. 2012; pp. 10-19.
Fontana RS et al.; "Lung Cancer Screening: The Mayo Program"; Journal of Occupational Medicine, vol. 28, No. 8; Aug. 1986; pp. 746-750.
Goldstraw P et al.; "The IASLC Lung Cancer Staging Project: Proposals for the Revision of the TNM Stage Groupings in the Forthcoming (Seventh) Edition of the TNM Classification of Malignant Tumours"; Journal of Thoracic Oncology, Vo. 2, No. 8; Aug. 2007; pp. 706-714.
Goulart BH et al.; "Lung Cancer Screening with Low-Dose Computed Tomography: Costs, National Expenditures, and Cost-Effectiveness"; Journal of the National Comprehensive Cancer Network, vol. 10, No. 2; Feb. 2012; pp. 267-275.
Groome PA et al.; The IASLC Lung Cancer Staging Project: Validation of the Proposals for Revision of the T, N, and M Descriptors and Consequent Stage Groupings in the Forthcoming (Seventh) Edition of the TNM Classification of Malignant Tumours; Journal of Thoracic Oncology, vol. 2, No. 8; Aug. 2007; pp. 694-705.
He et al.; "Proteomics-based identification of α-enolase as a tumor antigen in non-small lung cancer"; Cancer Science; vol. 98, No. 8; Aug. 2007; pp. 1234-1240.
Henschke CI et al.; "Survival of Patients with Stage I Lung Cancer Detected on CT Screening"; New England Journal of Medicine, vol. 355, No. 17; Oct. 26, 2006; pp. 1763-1771.
Henschke CI et al.; "CT Screening for Lung Cancer: Update 2007"; The Oncologist, vol. 13; Jan. 2008; pp. 65-78.
Jemal A et al.; "Cancer occurrence"; Methods in Molecular Biology, vol. 471: Abstract; 2009; pp. 3-29.
Jemal A. et al.; "Annual report to the nation on the status of cancer 1975-2005, featuring trends in lung cancer, tobacco use, and tobacco control"; J Natl Cancer Inst, vol. 100; Dec. 3, 2008; pp. 1672-1694.

Kaminska et al.; "Pretreatment Serum Levels of Cytokines and Cytokine Receptors in Patients with Non-Small Cell Lung Cancer, and Correlations with Clinicopathological Features and Prognosis"; Oncology, vol. 70; May 2006; pp. 115-125.
Kubik A et al.; "Lack of benefit from semi-annual screening for cancer of the lung: follow-up report of a randomized controlled trial on a population of high-risk males in Czechoslovakia"; International Journal of Cancer, vol. 45, Issue 1; Jan. 15, 1990; pp. 26-33.
Lai, Chun-Liang et al.; "Presence of Serum Anti-p53 Antibodies Is Associated with Pleural Effusion and Poor Prognosis in Lung Cancer Patients"; Clinical Cancer Research, vol. 4; Dec. 1998; pp. 3025-3030.
MacMahon H et al.; "Guidelines for Management of Small Pulmonary Nodules Detected on CT Scans: A Statement from the Fleischner Society"; Radiology; Nov. 2005; pp. 395-400.
Melamed MR et al.; "Screening for early lung cancer. Results of the Memorial Sloan-Kettering Study in New York"; Chest; Jul. 1984; pp. 44-53.
Murray A et al.; "Technical validation of an autoantibody test for lung cancer"; Annals of Oncology, vol. 21, No. 8; Aug. 2010; pp. 1687-1693.
Oken MM et al.; "Screening by Chest Radiograph and Lung Cancer Mortality: The Prostate, Lung, Colorectal, and Ovarian (PLCO) Randomized Trial"; Jama, vol. 306, No. 17; Nov. 2, 2011; pp. 1865-1873.
Pastor A et al.; "Diagnostic value of SCC, CEA and CYFRA 21.1 in lung cancer: a Bayesian analysis"; European Respiratory Journal, vol. 10, Issue 3; Mar. 1, 1997; pp. 603-609.
Patel K et al.; "Enhancement of a multianalyte serum biomarker panel to identify lymph node metastases in non-small cell lung cancer with circulating autoantibody biomarkers"; International Journal of Cancer, vol. 129, Issue 1; Jul. 1, 2011; pp. 133-142.
Patz EF, Jr. et al.; "National Lung Cancer Screening Trial American College of Radiology Imaging Network Specimen Biorepository originating from the Contemporary Screening for the Detection of Lung Cancer Trial (NLST, ACRIN 6654): Design, Intent, and Availability of Specimens for Validation of Lung Cancer Biomarkers"; Journal of Thoracic Oncology, vol. 5, No. 10; Oct. 2011; pp. 1502-1506.
Port JL et al.; "Tumor Size Predicts Survival Within Stage IA Non-Small Cell Lung Cancer"; Chest, vol. 124, No. 5; Nov. 2003; pp. 1828-1833.
SDF-1 Antibody Fact Sheet; Bio-Rad; 2016; 5 pages; https://www.bio-rad-antibodies.com/human-sdf-1-alpha-antibody-ahp794.html last visited Jul. 22, 2016.
Seike, Masahiro et al.; "Use of a Cytokine Gene Expression Signature in Lung Adenocarcinoma and the Surrounding Tissue as a Prognostic Classifier"; Journal of the National Cancer Institute, vol. 99, No. 16; Aug. 15, 2007; pp. 1257-1269.
Shersher, David D. et al.; "Biomarkers of the Insulin-Like Growth Factor Pathway Predict Progression and Outcome in Lung Cancer"; Ann Thorac Surg, vol. 92; Jun. 2011; pp. 1805-1811.
Vercillo, M. et al.; "A multi-analyte serum test for the early diagnosis of non-small cell lung cancer"; Journal of Clinical Oncology, vol. 28, No. 15, Supplement; May 20, 2010; p. 1554; Abstract.
Wald et al.; "CD4+CXCR4highCD69+ T Cells Accumulate in Lung Adenocarcinoma"; Journal of Immunology; vol. 177; Nov. 15, 2006; pp. 6983-6990.
Zhu et al.; "Immunohistochemical markers of prognosis in non-small cell lung cancer: a review and proposal for a multiphase approach to marker evaluation"; Journal of Clinical Pathology, vol. 59; Aug. 2006; pp. 790-800.
International Search Report completed Feb. 10, 2015 for International Application No. PCT/US2014/069009.
Written Opinion completed Feb. 10, 2015 for International Application No. PCT/US2014/069009.
Borgia et al.; "Correlation of angiogenesis biomarkers with early metastatic progression in NSCLC as determined using a multiplexed immunoassay kit"; EMD Millipore White Paper; retrieved from the Internet on May 4, 2017 at https://www.scribd.com/document/93946404/Correlation-of-anqioqenesis-biomarkers-with-early-metastatic-progression-in-NSCLC; XP002769864; 2012; pp. 1-8.

(56) References Cited

OTHER PUBLICATIONS

Heemann et al.; "Circulating levels of TNF-receptor II are prognostic for patients with peripheral T-cell Non-Hodgkin lymphoma"; downloaded from clincancerres.aacrjournals.org on May 4, 2017; May 9, 2012; 28 pages.
Supplementary European Search Report completed May 5, 2017 for European Application No. EP 14 86 9355.

\* cited by examiner

BIOMARKERS OF RAPID PROGRESSION IN ADVANCED NON-SMALL CELL LUNG CANCER

RELATED APPLICATIONS

This application claims the benefit under 35 U.S.C. § 371 of International Application No. PCT/US2014/069009, filed Dec. 8, 2014, which claims the benefit of U.S. Provisional Application No. 61/913,740, filed Dec. 9, 2013, which are incorporated by reference herein in their entirety.

TECHNICAL FIELD

The present invention relates to methods and kits for identifying patients with rapidly progressing disease, and in particular to methods and kits for identifying patients with rapidly progressing non-small cell lung cancer and for determining optimal treatment plans for patients with rapidly progressing disease and for monitoring treatments.

BACKGROUND

Lung cancer is leading cause of cancer-related mortality worldwide, with a projected 159,480 patients succumbing to the disease in the US in 2014.(1) Lung cancer is typically characterized as being quite aggressive with poor clinical outcomes that stem from the very rapid proliferation rates, high metastatic potential, and general insensitivity to available treatment strategies. Non-small cell lung cancer (NSCLC) presents unique challenges to health care providers because of its common late stage of presentation and the poor median overall survival of advanced disease.(2, 3) Patients often become too ill to receive second line treatment as noted by a recent phase III clinical trial where only 37% of the patients randomized to docetaxel at disease progression received treatment.(4)

An objective of this study was reveal circulating biomarkers to identify patients with rapidly progressing NSCLC. This study examined 76 biomarkers that are surrogates for several pathophysiological processes associated with aggressive disease in both frontline (chemo naïve) and second-line and greater (pretreated) patients. A total of 186 patient serum specimens were evaluated. Processes evaluated include angiogenesis, phenotypic transdifferentiation (i.e. EMT, cancer stem cells), cancer cachexia, chronic inflammation, and immune system response.

Identification of patients with rapidly-progressing disease who are insensitive to standard platinum double-based chemotherapy will provide clinical implications.

There is a need in the art for screening methods and kits that identify patients with rapidly progressing disease in patients that are treatment naïve and in patients that have received a treatment.

BRIEF SUMMARY

Methods and kits for identifying rapidly progressing lung cancer in a subject are provided. The method includes obtaining a biological sample from the subject and assaying a level of a biomarker in a biomarker panel in the biological sample where the panel includes at least one biomarker selected from Table I or Table II. The method is dependent on whether the subject is treatment naïve or has received at least one treatment; and comparing the level of the biomarker in the subject's sample to a cutoff value listed in Table I for treatment naïve subjects or Table II for previously treated subjects. The method further includes determining whether the subject's level is above or below the cutoff value to determine whether the subject has rapidly progressing lung cancer.

DETAILED DESCRIPTION

Figures 1A, 1B:
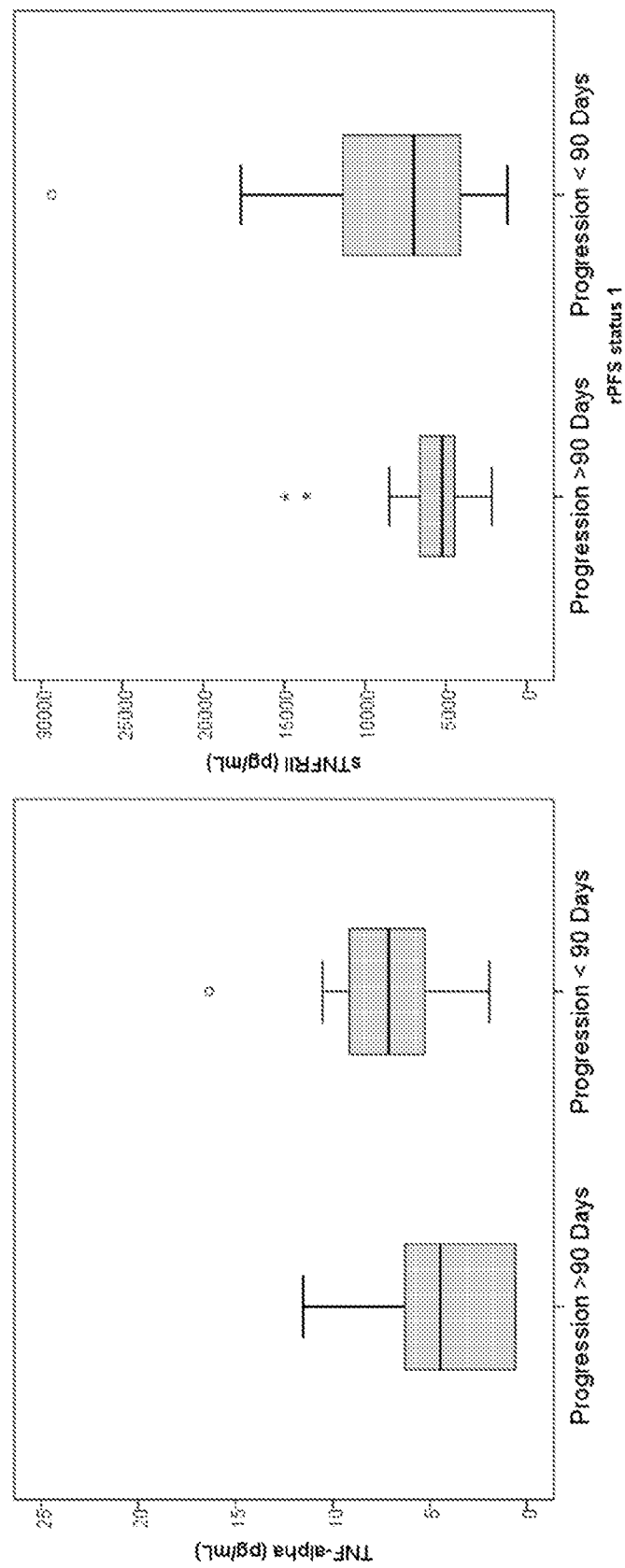
FIG. 1 illustrates representative 'Box and Whisker' plots indicating distribution of biomarker levels in the frontline chemotherapy cohort, separated based on a 90 day cutoff for rapid disease progression. Shown are TNF-α (panel A), sTNFRII (panel B), IL-6 (panel C), sVEGFR3 (panel D), betacellulin (Panel E) and Total PSA (panel F). All biomarker levels are provided in pg/mL.

The present invention will utilize at least one biomarker measured in a biological sample obtained from a subject to identify rapidly progressing lung cancer, and in some embodiments in subjects having rapidly progressing NSCLC. In some embodiments, the at least one biomarker may be selected from a panel of biomarkers. In some embodiments, one or more biomarkers from a panel of biomarkers are used to identify subjects having rapidly progressing NSCLC in subjects that are treatment naïve or that have been previously treated.

The term "biomarker" as used herein, refers to any biological compound that can be measured as an indicator of the physiological status of a biological system. A biomarker may comprise an amino acid sequence, a nucleic acid sequence and fragments thereof. Exemplary biomarkers include, but are not limited to cytokines, chemokines, growth and angiogenic factors, metastasis related molecules, cancer antigens, apoptosis related proteins, proteases, adhesion molecules, cell signaling molecules and hormones.

"Measuring" or "measurement" means assessing the presence, absence, quantity or amount (which can be an effective amount) of a given substance within a sample, including the derivation of qualitative or quantitative concentration levels of such substances, or otherwise evaluating the values or categorization of a subject's clinical parameters. Alternatively, the term "detecting" or "detection" may be used and is understood to cover all measuring or measurement as described herein.

The terms "sample" or "biological sample" as used herein, refers to a sample of biological fluid, tissue, or cells, in a healthy and/or pathological state obtained from a subject. Such samples include, but are not limited to, blood, bronchial lavage fluid, sputum, saliva, urine, amniotic fluid, lymph fluid, tissue or fine needle biopsy samples, peritoneal fluid, cerebrospinal fluid, and includes supernatant from cell lysates, lysed cells, cellular extracts, and nuclear extracts. In some embodiments, the whole blood sample is further processed into serum or plasma samples. In some embodiments, the sample includes blood spotting tests.

The term "subject" or "patient" as used herein, refers to a mammal, preferably a human.

The term "rapid progression" or "rapidly progressing" as used herein, refers to cases of disease that were observed to not respond to chemotherapy or targeted agents and advance (evidence of nascent metastases, increasing tumor volume, etc.) within a defined time interval. Thresholds for rapid progression were set to 90 days after the first treatment for the treatment naïve patients and 45 days after the second or subsequent treatment for the previously treated patients. Circulating levels of 27 biomarkers were found to be significantly associated (p≤0.05) with progression within 90 days of treatment initiation in treatment naive patients. Circulating levels of 34 biomarkers were found to be significantly associated (p≤0.05) with progression within 45 days of treatment initiation in previously treated patients.

Biomarkers

Biomarkers that may be used include but are not limited to cytokines, chemokines, growth and angiogenic factors, metastasis related molecules, cancer antigens, apoptosis related proteins, proteases, adhesion molecules, cell signaling molecules and hormones. In some embodiments, the biomarkers may be proteins that are circulating in the subject that may be detected from a fluid sample obtained from the subject. In some embodiments, the fluid sample may be serum or plasma. In some embodiments, one or more biomarkers from a panel of biomarkers may be used.

In some embodiments, one or more biomarkers may be measured in a biomarker panel. The biomarker panel may include a plurality of biomarkers. In some embodiments, the biomarker panel may include ten or fewer biomarkers. In yet other embodiments, the biomarker panel may include 1, 2, 3, 4, 5, 6 or 7 biomarkers. In some embodiments, the biomarker panel may be optimized from a candidate pool of biomarkers. By way of non-limiting example, the biomarker or biomarker panel may be configured for determining whether a treatment naïve subject is likely to have rapidly progressing disease. In some embodiments, the biomarker or biomarker panel may be configured for determining whether a previously treated subject is likely to have rapidly progressing disease.

In some embodiments, the biomarker panel may include biomarkers from several biological pathways. By way of non-limiting example, the biomarkers may be associated the tumor necrosis factor (TNF) family, the epidermal growth factor (EGF) family, the vascular endothelial growth factor (VEGF) family, the Insulin-like growth factor (IGF) family and/or associated with angiogenesis. In some embodiments, the TNF family may include, but is not limited to TNF-RI, TNF-RII, TNF-α and TRAIL. In some embodiments, the EGF family may include but is not limited to betacellulin, amphiregulin, and soluble-EGFR. In some embodiments, the VEGF family may include but is not limited to VEGF-A, VEGF-C, and soluble-VEGFR3. In some embodiments, the IGF family may include but is not limited to IGF-I, IGF-II, IGFBPs-2,-3, and -7. In some embodiments, the biomarkers associated with angiogenesis may include follistatin, IL-6, endoglin, PDGF-BB, IGF-1, and endothelin-1, PLGF, IL-8, MMP-2, HGF, sVEGFR2, VEGF-A, leptin, PDGF-AA, and others. In some embodiments, the biomarker panel may include one or more biomarkers from a panel of biomarkers. In some embodiments, the one or more biomarkers may be selected from the list of biomarkers in Table I. In some embodiments, the one or more biomarkers may be selected from the list of biomarkers in Table II. In some embodiments, other biomarkers may be used and may be combined with the biomarkers listed in Tables I and II.

In some embodiments, patients with rapid disease progression in a treatment naïve group may be identified using one or more biomarkers selected from a panel of biomarkers listed Table I. In some embodiments, the one or more biomarkers may be selected from the group of biomarkers identified in Table I as having a p-value of 0.01 or less. In some embodiments, the one or more biomarkers may include at least one biomarker from Table I having a p-value of 0.01 or less and at least one biomarker from Table I having a p-value of 0.05 or less. In some embodiments, the one or more biomarkers may include biomarkers selected from the group consisting of sTNFRI, sTNFRII, CA 19-9, Follistatin, Total PSA, TNF-α and IL-6. In some embodiments, the biomarkers may include 3, 4, 5, 6 or 7 biomarkers selected from the group consisting of sTNFRI, sTNFRII, CA 19-9, Follistatin, Total PSA, TNF-α and IL-6 and may also include additional biomarkers. In some embodiments, patients with rapid disease progression in a treatment naïve group may be identified using a panel of one or more biomarkers selected from Table I where the panel may include 1, 2, 3, 4, 5, 6, 7, 8, 9, 10, 11, 12, 13, 14, 15, 16, 17, 18, 19, 20, 21, 22, 23, 24, 25, 26 or 27 biomarkers.

In some embodiments, patients with rapid disease progression in a previously treated group may be identified using one or more biomarkers selected from a panel of biomarkers selected from Table II. In some embodiments, the one or more biomarkers may be selected from the group of biomarkers identified in Table II as having a p-value of 0.01 or less. In some embodiments, the one or more biomarkers may include at least one biomarker from Table II having a p-value of 0.01 or less and at least one biomarker form Table II having a p-value of 0.05 or less. In some embodiments, the one or more biomarkers may be selected from the group consisting of TRAIL, sTNFRI, IGFBP-1, sEGFR, IGF-1, TGF-β, HGF, MMP-7, MMP-2, a-fetoprotein, Osteopontin, sVEGFR2 and IL-6. In some embodiments, the one or more biomarkers may include 1, 2, 3, 4, 5, 6, 7, 8, 9, 10, 11, 12 or 13 biomarkers selected from the group consisting of TRAIL, sTNFRI, IGFBP-1, sEGFR, IGF-1, TGF-β, HGF, MMP-7, MMP-2, a-fetoprotein, Osteopontin, sVEGFR2 and IL-6 and may also include additional biomarkers. In some embodiments, patients with rapid disease progression in a previously treated group may be identified using one or more biomarkers selected from Table II where the panel may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 biomarkers.

In some embodiments, the biomarker panel may be selected using a reference profile that can be made in conjunction with a statistical algorithm used with a computer to implement the statistical algorithm to sort the subject into a group. In some embodiments, the statistical algorithm is a learning statistical classifier system. The learning statistical classifier system can be selected from the following list of non-limiting examples, including Random Forest (RF), Classification and Regression Tree (CART), boosted tree, neural network (NN), support vector machine (SVM), general chi-squared automatic interaction detector model, interactive tree, multiadaptive regression spline, machine learning classifier, and combinations thereof. By way of non-limiting example, exemplary tools for selecting a biomarker panel may be found in WO 2012/054732 and U.S. Provisional Application No. 61/792,710 which are incorporated by reference herein.

Biomarker Measurement

Measurement of a biomarker generally relates to a quantitative measurement of an expression product, which is typically a protein or polypeptide. In some embodiments, the measurement of a biomarker may relate to a quantitative or qualitative measurement of nucleic acids, such as DNA or RNA. The measurement of the biomarker of the subject detects expression levels of one or more biomarkers in subjects having lung cancer and in some embodiments, compares the expression level of each biomarker measured to a cutoff value listed in Table I or in Table II.

Expression of the biomarkers may be measured using any method known to one skilled in the art. Methods for measuring protein expression include, but are not limited to Western blot, immunoprecipitation, immunohistochemistry, Enzyme-linked immunosorbent assay (ELISA), Radio Immuno Assay (RIA), radioreceptor assay, proteomics methods, mass-spectrometry based detection (SRM or MRM) or quantitative immunostaining methods. Methods for measuring nucleic acid expression or levels may be any techniques known to one skilled in the art. Expression levels from the one or more biomarkers are measured in the subject and compared to the levels of the one or more biomarkers obtained from a cohort of subjects described below.

In some embodiments, MILLIPLEX® MAP multiplex assays may be used to determine the expression levels of the one or more biomarkers in a panel of biomarkers. (EMD Millipore, Billlerica, MA.) In some embodiments, Luminex-based xMAP® multiplexed immunoassays may be used to determine the expression levels of the panel of biomarkers. (Luminex Corp.; Austin, Tex.) In some embodiments, biomarker concentrations may be calculated based on 7-point standard curves using a five-parametric fit algorithm in xPONENT v4.0.3 (Luminex Corp.) Other measurement systems and techniques may also be used.

In some embodiments, a kit may be provided with reagents to measure at least one biomarker. In some embodiments, the kit may be provided with reagents to measures at least two biomarkers in a panel of biomarkers. The panel of biomarkers to be measured with the kit may include two or more biomarkers from Table I or Table II. The kit may include reagents to measure a panel of biomarkers for subjects that are treatment naïve. The kit may include reagents to measure a panel of biomarkers for subjects that have been previously treated.

Analysis of Biomarker Measurements

In some embodiments, methods for determining whether a subject has rapidly progressing lung cancer may be based upon the biomarker measurements from the subject compared to a reference cutoff level for each biomarker measured. The reference cutoff level for a plurality of biomarkers is listed in Tables I-IV.

Treatment Stratification

In some embodiments, the analysis of the biomarker panel may be used to determine a treatment regime for the subject. In some embodiments, the measurement of one or more biomarkers in the panel may be used to determine whether to begin a treatment, to continue the same treatment or to modify the treatment regime for a subject. The treatment may be modified by changing the drug administered to the subject or to add an additional drug to the existing drug treatment regime, to change the dosage or other changes. In some embodiments, other types of treatment regimes may be used such as radiation. In some embodiments, the identification of patients with rapidly progressing disease who are insensitive to standard platinum doublet-based chemotherapy may have multiple clinical implications. The identification of patients with rapidly progressing disease using the biomarker level may place the patient in a specific treatment, a different treatment or an earlier treatment in the overall treatment strategy. In some embodiments, a specific targeted chemotherapeutic agent may be selected based on the identification of rapidly progressing disease. In some embodiments, the specific chemotherapeutic agent may be changed based in the biomarker level measured relative to the cutoff value. By way of non-limiting example, VEGF-A levels in patients taking bevacizumab may be monitored and the treatment regime may be changed or not changed based on the level of VEGF-A measured and compared to the cutoff level in either Table I for treatment naïve patients or Table II for previously treated patients.

Patient Cohorts

Between 2004 and 2011, 186 patients at Rush University Medical Center (Chicago, Ill.) were enrolled and divided into the following cohorts: patients with advanced lung adenocarcinoma naïve to previous chemotherapy (n=76) and patients with advanced lung adenocarcinoma that have failed at least 1 line of chemotherapy (n=110). All stage classifications were determined according to the American Joint Committee on Cancer (AJCC) seventh edition criteria and confirmed by pathological evaluation (5, 6). All patient data was obtained after informed consent was given by the patient. The study was conducted in absolute compliance with the Institutional Review Board at Rush University Medical Center.

Measurement of Serum Biomarker Concentrations

All peripheral blood was collected pre-treatment and processed into serum using standard phlebotomy protocols. Serum was archived at −80° C. in aliquots; and no evaluable specimen were subjected to more than two freeze-thaw cycles (7-10). Serum was evaluated using the following biomarker panels: the MILLIPLEX® MAP Human Angiogenesis/Growth Factor Panel (EMD Millipore, Billerica, Mass.) and included the following assays: epidermal growth factor (EGF), angiopoietin-2, granulocyte colony-stimulating factor (G-CSF), bone morphogenic protein 9 (BMP-9), endoglin, endothelin-1, leptin, fibroblast growth factor-1 (FGF-1), FGF-2, follistatin, interleukin-8 (IL-8), hepatocyte growth factor (HGF), heparin-binding epidermal growth factor (HB-EGF), placental growth factor (PLGF), vascular endothelial growth factor-A (VEGF-A), VEGF-C and VEGF-D; the MILLIPLEX® MAP Human Soluble Cytokine Receptor Panel which includes sVEGFR1, sVEGFR2, sVEGFR3, sIL-6R, sgp130, sTNFRI, and sTNFRII; the MILLIPLEX® MAP Human Circulating Cancer Biomarker Panel 1 which includes sFasL, IL-6, prolactin, SCF, TGF-α, and TNF-α; the MILLIPLEX® MAP Human MMP1 and MMP2 panels which combine to provide MMPs -1,-2,-3,-7,-9, and -10; and the MILLIPLEX® MAP Human Cytokine/Chemokine Panel II, which includes SDF-1 (α+β). All assays were performed according to the manufacturer's recommended protocols and in a blinded fashion. All data was collected on a Luminex FlexMAP 3D system with concentrations calculated based on 7-point standard curves using a five-parametric fit algorithm in xPONENT v4.0.3 (Luminex Corp., Austin, Tex.).

Statistical Methods

One endpoint of the investigation was to evaluate associations of the circulating biomarkers tested with clinical outcome measures for patients determined to have rapidly progressing disease. Progression status values were classified as 'slow' or 'rapid' based on chosen clinically-relevant cutoff (45 days for frontline and 90 days for those second-line and above) value. Association of the slow/rapid progression state was then accomplished with low and high values of a biomarker based on cutoff values obtained from a grid search for an optimal cutoff within the potential range of the biomarker values that maximizes the p-value for disease progression via Fisher's exact test. Additionally, an adjusted p-value, which adjusts for the grid search, is also obtained. These analyses were performed regardless of regimen type. All statistical analyses were completed using the R Statistical Package.

Results

Frontline Treatment for Advanced NSCLC

Figure 1D:
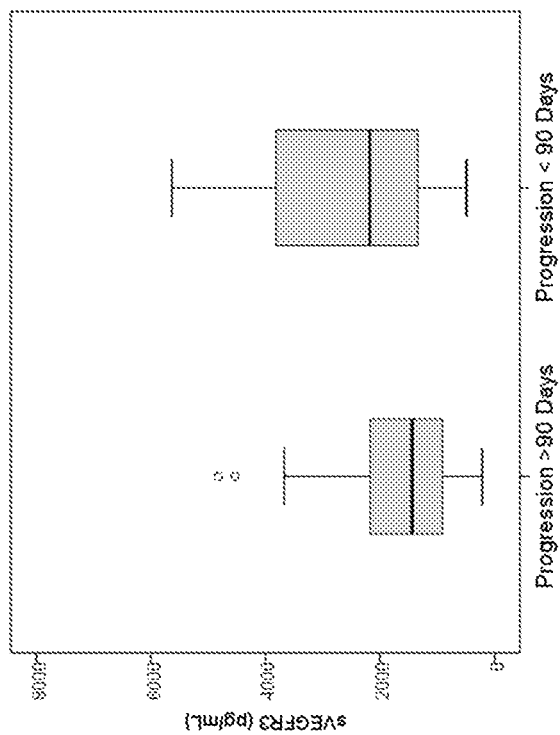
Figure 1C:
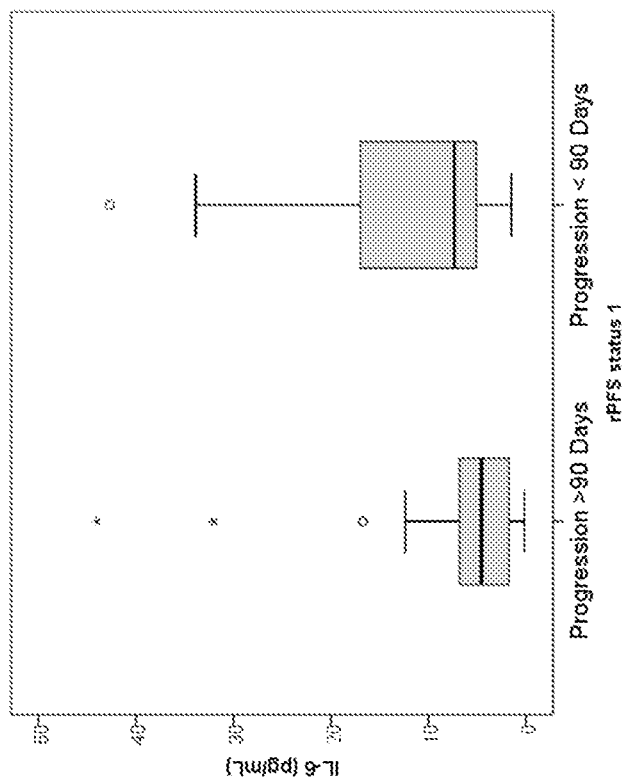
Figure 1F:
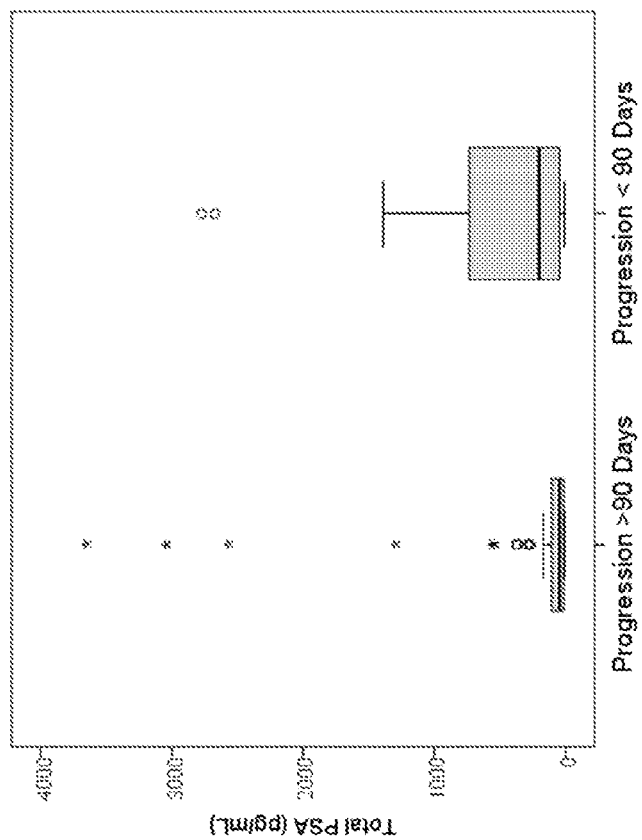
Figure 1E:
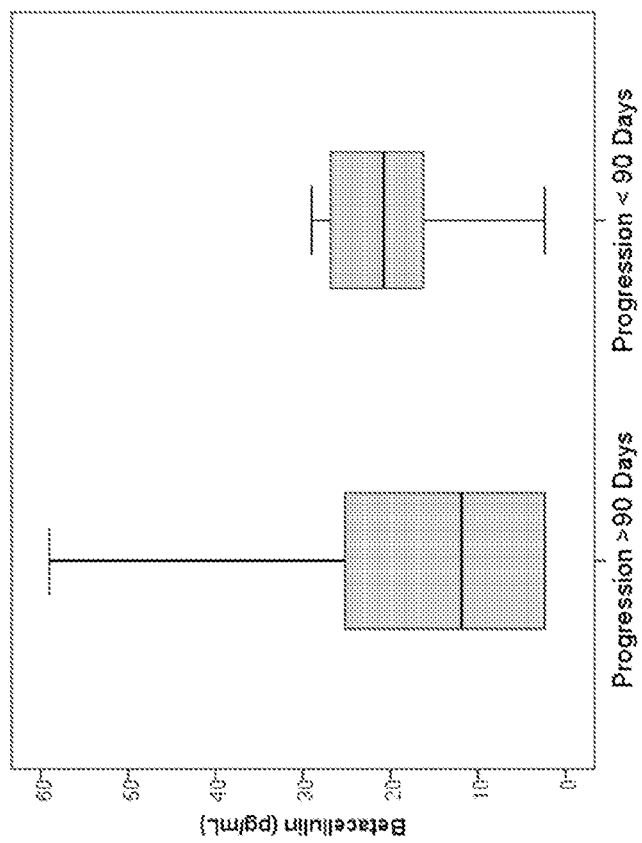

A total of 27 biomarkers were identified for identifying advanced stage NSCLC patients that were chemotherapy naïve with rapidly progressing disease. The specific cutoff values, number of patients in each arm, and optimal p-values are all provided in Table I, with the distribution of these classifications for select representative biomarkers provided in FIG. 1. A complete account for all 76 biomarkers is provided in Table III. Included in the findings were biomarkers with optimal p-value 5.0.05 representing the following processes: angiogenesis (sTNFRI, sTNFRII, Follistatin, TNF-α, Betacellulin, sVEGFR3, VEGF-A, Endoglin, MMP-10, PDGF-BB, VEGF-C, IGF-I, IGFBP-3, IGFBP-5, Endothelin-1, and Amphiregulin), cancer cachexia (TNF-α, sTNFRI, sTNFRII, IGF-I, IGFBP-3, IGFBP-5, IL-6, IL-6R), and phenotypic transdifferentiation (betacellulin, IGF-I, IGFBP-3, IGFBP-5, sEGFR, and prolactin).

Previous Treatment for Advanced NSCLC

Figure 2B:
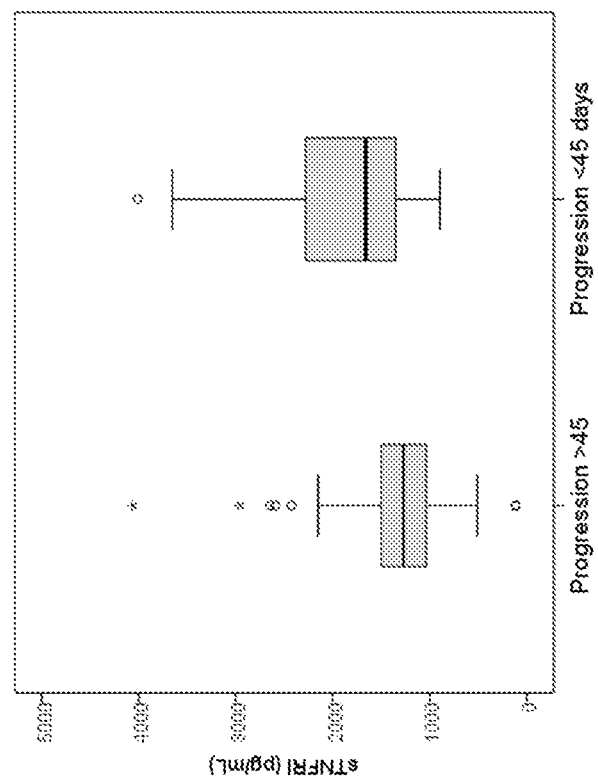
FIG. 2 illustrates representative 'Box and Whisker' plots indicating distribution of biomarker levels in the treated chemotherapy cohort, separated based on a 45 day cutoff for rapid disease progression. Shown are sEGFR (panel A), sTNFRI (panel B), TRAIL (panel C), IGFBP-1 (panel D), IGFBP-2 (Panel E) and HGF (panel F). All biomarker levels are provided in pg/mL.
Figure 2A:
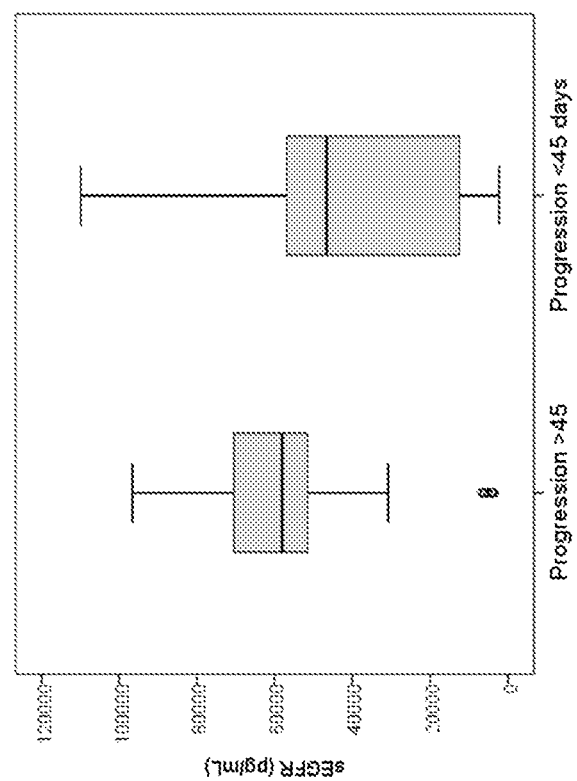
Figure 2D:
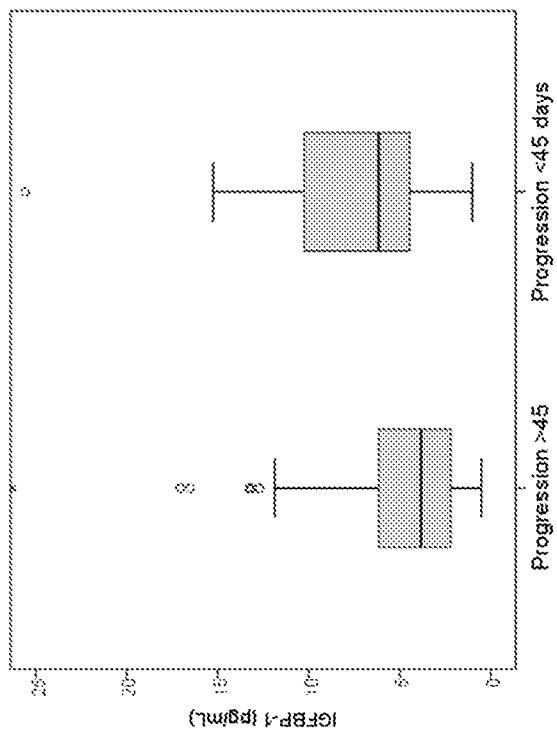
Figure 2C:
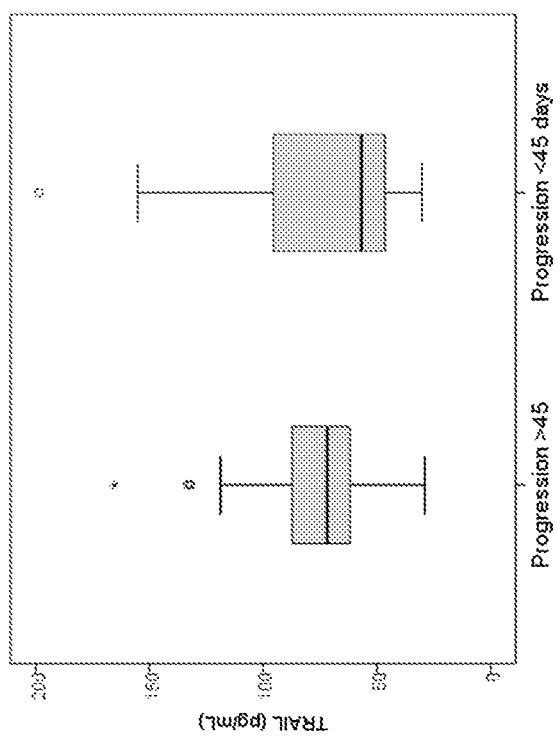
Figure 2E:
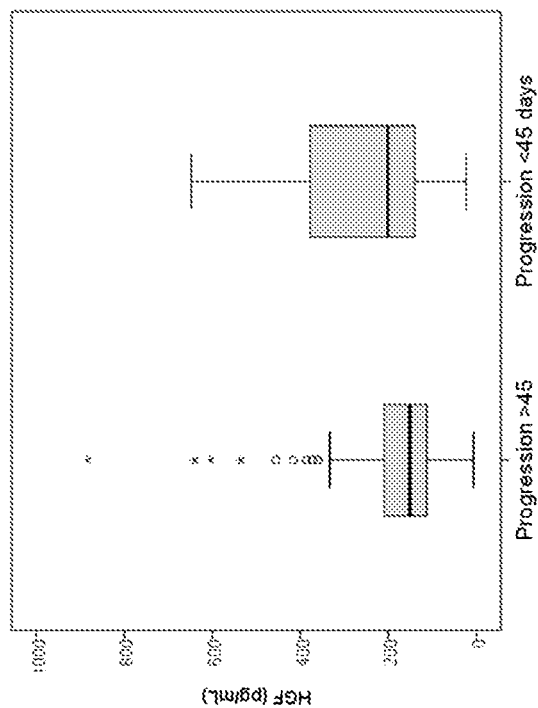
Figure 2F:
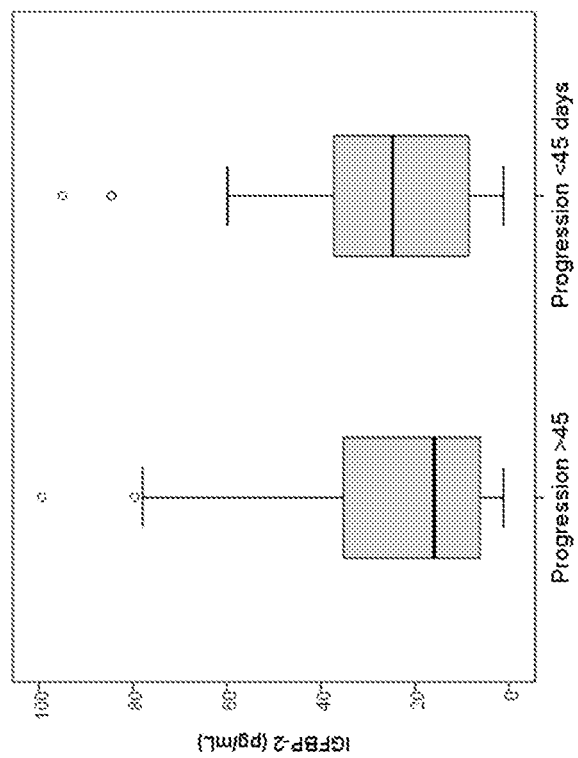

A total of 34 biomarkers were identified for identifying advanced stage NSCLC patients that failed frontline chemotherapy with rapidly progressing disease. The specific cutoff values, number of patients in each arm, and optimal p-values are all provided in Table II, with the distribution of these classifications for select representative biomarkers provided in FIG. 2. A complete account for all 76 biomarkers are provided in Table IV. Included in the findings were biomarkers with optimal p-value 50.05 representing the following processes: angiogenesis (sVEGFR2, follistatin, IGF-I, IGF-II, IGFBPs -1,-2,-3,-5,-7, IL-8, MMP-2, MMP-7, PLGF, Leptin, PDGF-AA, TNF-α, sTNFRI, sTNFRII, and VEGF-A), cancer cachexia (HGF, IGF-I, IGF-II, IGFBPs -1,-2,-3,-5,-7, IL-6, Leptin, TRAIL, sCD30, TNF-α, sTNFRI, and sTNFRII), phenotypic transdifferentiation (beta-HCG, a-fetoprotein, HE4, HGF, IGF-I, IGF-II, IGFBPs -1,-2,-3,-5,-7, osteopontin, PLGF, TGF-β, and sEGFR), and inflammation or immune response (CYFRA 21-1, GRO, IL-6, IL-8, sIL-2Ra, sIL-4R, TRAIL, sCD30, TNF-α, sTNFRI, and sTNFRII).

TABLE I

Treatment Naïve Cohort

| Biomarker | Cutoff Value (pg/mL) | Cases ≤ cutoff | Cases > Cutoff | p-Value | Adjusted p-value |
|---|---|---|---|---|---|
| sTNFRI | 1879.8 | 48 | 12 | 0.0003 | 0.001 |
| sTNFRII | 8493.9 | 49 | 11 | 0.0011 | 0.006 |
| CA 19-9 | 20.9 | 62 | 13 | 0.0029 | 0.018 |
| Follistatin | 990.0 | 48 | 15 | 0.0033 | 0.007 |
| Total PSA | 67.1 | 47 | 28 | 0.0042 | 0.027 |
| TNF-α | 0.61 | 12 | 45 | 0.0050 | 0.029 |
| IL-6 | 13.1 | 48 | 10 | 0.0100 | 0.021 |
| TGF β1 | 30665.9 | 64 | 11 | 0.0132 | 0.083 |
| Betacellulin | 14.9 | 25 | 28 | 0.0162 | 0.058 |
| CA 15.3 | 55.0 | 62 | 13 | 0.0203 | 0.077 |
| sCD30 | 101.5 | 40 | 20 | 0.0219 | 0.111 |
| sVEGFR3 | 2930.8 | 48 | 12 | 0.0221 | 0.094 |
| VEGF-A | 727.1 | 49 | 27 | 0.0222 | 0.092 |
| Endoglin | 993.8 | 48 | 15 | 0.0228 | 0.084 |
| MMP-10 | 272.6 | 43 | 32 | 0.0244 | 0.122 |
| sRAGE | 84.2 | 39 | 21 | 0.0244 | 0.121 |
| PDGF-BB | 13336.6 | 12 | 40 | 0.0248 | 0.075 |
| VEGF-C | 32.9 | 10 | 53 | 0.0255 | 0.105 |
| IGF-I | 31266.8 | 46 | 30 | 0.0264 | 0.133 |
| IGFBP-3 | 1452.8 | 53 | 23 | 0.0308 | 0.168 |
| sEGFR | 25073.2 | 29 | 43 | 0.0392 | 0.177 |
| IGFBP-5 | 151.1 | 48 | 28 | 0.0428 | 0.192 |
| Endothelin-1 | 8.0 | 39 | 24 | 0.0430 | 0.124 |
| Amphiregulin | 38.7 | 16 | 36 | 0.0445 | 0.222 |
| GRO | 3960.3 | 47 | 28 | 0.0453 | 0.181 |
| sIL-6R | 10666.7 | 20 | 40 | 0.0493 | 0.203 |
| Prolactin | 5353.7 | 30 | 28 | 0.0497 | 0.152 |

TABLE II

Post Treatment Cohort

| Biomarker | Cutoff Value (pg/mL) | Cases ≤ cutoff | Cases > Cutoff | p-Value | Adjusted p-value |
|---|---|---|---|---|---|
| TRAIL | 60.3 | 35 | 76 | 0.0005 | 0.003 |
| sTNFRI | 1506.6 | 62 | 34 | 0.0007 | 0.005 |
| IGFBP-1 | 9.2 | 88 | 22 | 0.0009 | 0.005 |
| sEGFR | 50565.2 | 36 | 68 | 0.0012 | 0.007 |
| IGF-I | 7807.7 | 32 | 78 | 0.0021 | 0.008 |
| TGF-β1 | 9073.7 | 10 | 77 | 0.0028 | 0.016 |
| HGF | 239.7 | 81 | 30 | 0.0035 | 0.034 |
| MMP-7 | 8326.9 | 68 | 43 | 0.0043 | 0.024 |
| MMP-2 | 33782.5 | 31 | 80 | 0.0044 | 0.027 |
| α-fetoprotein | 964.1 | 63 | 40 | 0.0050 | 0.031 |
| Osteopontin | 34067.2 | 49 | 54 | 0.0058 | 0.034 |
| sVEGFR2 | 10846.5 | 13 | 83 | 0.0073 | 0.049 |
| IL-6 | 8.0 | 66 | 37 | 0.0098 | 0.035 |
| CYFRA 21.1 | 768.7 | 51 | 52 | 0.0119 | 0.03 |
| IGF-II | 507.7 | 37 | 68 | 0.0129 | 0.083 |
| sTNFRII | 7588.9 | 65 | 31 | 0.0151 | 0.093 |
| CA 15.3 | 34.5 | 83 | 28 | 0.0156 | 0.056 |
| sCD30 | 129.7 | 73 | 23 | 0.0177 | 0.081 |
| sIL-4R | 2096.7 | 14 | 82 | 0.0201 | 0.103 |
| sIL-2Ralpha | 836.6 | 55 | 41 | 0.0208 | 0.118 |
| IGFBP-7 | 53.7 | 18 | 92 | 0.0211 | 0.137 |
| TNF-α | 91.1 | 93 | 17 | 0.0213 | 0.114 |
| VEGF-A | 1297.7 | 98 | 14 | 0.0227 | 0.05 |
| Follistatin | 968.9 | 11 | 10 | 0.0237 | 0.013 |
| Leptin-1 | 11840.0 | 55 | 48 | 0.0239 | 0.154 |
| IGFBP-3 | 1486.8 | 90 | 20 | 0.0263 | 0.161 |
| PLGF | 86.8 | 69 | 10 | 0.0268 | 0.127 |
| IGFBP-5 | 193.5 | 44 | 66 | 0.0296 | 0.166 |
| GRO | 4254.6 | 80 | 30 | 0.0333 | 0.162 |
| IL-8 | 63.9 | 96 | 15 | 0.0334 | 0.178 |
| HE4 | 2993.4 | 88 | 23 | 0.0343 | 0.201 |
| IGFBP-2 | 22.9 | 64 | 46 | 0.0344 | 0.169 |
| PDGF-AA | 10851.4 | 12 | 98 | 0.0375 | 0.218 |
| B-HCG | 0.16 | 26 | 85 | 0.0446 | 0.239 |

TABLE III

Treatment Naïve Cohort

| Biomarker | Cutoff | Prop. ≤ cutoff | No. ≤ Cutoff | Prop. > cutoff | No. > Cutoff | Total No. | Optimal p-value | Adjusted p-value |
|---|---|---|---|---|---|---|---|---|
| sTNFRI | 1879.789 | 0.75 | 48 | 0.166667 | 12 | 60 | 0.000344 | 0.001 |
| sTNFRII | 8493.872 | 0.734694 | 49 | 0.181818 | 11 | 60 | 0.001094 | 0.006 |
| CA.19.9 | 20.91498 | 0.758065 | 62 | 0.307692 | 13 | 75 | 0.00293 | 0.018 |
| Follistatin | 990.0075 | 0.625 | 48 | 1 | 15 | 63 | 0.003303 | 0.007 |
| Total.PSA | 67.1 | 0.808511 | 47 | 0.464286 | 28 | 75 | 0.004239 | 0.027 |

TABLE III-continued

Treatment Naïve Cohort

| Biomarker | Cutoff | Prop. ≤ cutoff | No. ≤ Cutoff | Prop. > cutoff | No. > Cutoff | Total No. | Optimal p-value | Adjusted p-value |
|---|---|---|---|---|---|---|---|---|
| TNF.alpha | 0.614 | 1 | 12 | 0.577778 | 45 | 57 | 0.005026 | 0.029 |
| IL.6 | 13.09553 | 0.75 | 48 | 0.3 | 10 | 58 | 0.009969 | 0.021 |
| TGF.beta1 | 30665.91 | 0.625 | 64 | 1 | 11 | 75 | 0.013211 | 0.083 |
| Betacellulin | 14.915 | 0.88 | 25 | 0.571429 | 28 | 53 | 0.016219 | 0.058 |
| CA.15.3 | 55.03582 | 0.741935 | 62 | 0.384615 | 13 | 75 | 0.020338 | 0.077 |
| sCD30 | 101.452 | 0.525 | 40 | 0.85 | 20 | 60 | 0.021891 | 0.111 |
| sVEGFR3 | 2930.841 | 0.708333 | 48 | 0.333333 | 12 | 60 | 0.022146 | 0.094 |
| VEGF | 727.1049 | 0.591837 | 49 | 0.851852 | 27 | 76 | 0.02221 | 0.092 |
| Endoglin | 993.8066 | 0.791667 | 48 | 0.466667 | 15 | 63 | 0.022804 | 0.084 |
| MMP.10 | 272.6212 | 0.790698 | 43 | 0.53125 | 32 | 75 | 0.024406 | 0.122 |
| SRAGE | 84.19616 | 0.74359 | 39 | 0.428571 | 21 | 60 | 0.024413 | 0.121 |
| PDGF.BB | 13336.56 | 0.416667 | 12 | 0.8 | 40 | 52 | 0.024825 | 0.075 |
| VEGF.C | 32.93148 | 0.4 | 10 | 0.773585 | 53 | 63 | 0.025532 | 0.105 |
| IGF.1 | 31266.81 | 0.586957 | 46 | 0.833333 | 30 | 76 | 0.026375 | 0.133 |
| IGFBP.3 | 1452.848 | 0.603774 | 53 | 0.869565 | 23 | 76 | 0.030829 | 0.168 |
| sEGFR | 25073.18 | 0.827586 | 29 | 0.581395 | 43 | 72 | 0.039227 | 0.177 |
| IGFBP.5 | 151.1263 | 0.770833 | 48 | 0.535714 | 28 | 76 | 0.042771 | 0.192 |
| Endothelin.1 | 8.012 | 0.615385 | 39 | 0.875 | 24 | 63 | 0.043036 | 0.124 |
| Amphiregulin | 38.666 | 0.5 | 16 | 0.805556 | 36 | 52 | 0.044476 | 0.222 |
| GRO | 3960.296 | 0.765957 | 47 | 0.535714 | 28 | 75 | 0.045349 | 0.181 |
| sIL.6R | 10666.72 | 0.45 | 20 | 0.725 | 40 | 60 | 0.049324 | 0.203 |
| Prolactin | 5353.744 | 0.8 | 30 | 0.535714 | 28 | 58 | 0.049721 | 0.152 |
| sIL.2Ralpha | 1390.342 | 0.702128 | 47 | 0.384615 | 13 | 60 | 0.051904 | 0.177 |
| FGF.2.1 | 77.31547 | 0.744186 | 43 | 0.466667 | 15 | 58 | 0.061694 | 0.192 |
| VEGF.D | 102.6913 | 0.782609 | 46 | 0.529412 | 17 | 63 | 0.063445 | 0.242 |
| PDGF.AA | 47558.59 | 0.607843 | 51 | 0.833333 | 24 | 75 | 0.065221 | 0.315 |
| Tenascin.C | 1130.558 | 0.84 | 25 | 0.592593 | 27 | 52 | 0.068469 | 0.207 |
| RANTES | 38837 | 0.821429 | 28 | 0.595745 | 47 | 75 | 0.071924 | 0.311 |
| IGFBP.4 | 19.09024 | 0.821429 | 28 | 0.604167 | 48 | 76 | 0.072878 | 0.299 |
| sIL.1RI | 61.50253 | 0.704545 | 44 | 0.4375 | 16 | 60 | 0.073962 | 0.299 |
| MIF | 192.023 | 0.875 | 16 | 0.627119 | 59 | 75 | 0.074126 | 0.225 |
| IGF.II | 304.3222 | 0.5 | 18 | 0.745455 | 55 | 73 | 0.078394 | 0.348 |
| Angiopoietin.2 | 2037.563 | 0.8 | 40 | 0.565217 | 23 | 63 | 0.080545 | 0.237 |
| VEGF.A | 383.2805 | 0.785714 | 42 | 0.571429 | 21 | 63 | 0.086763 | 0.279 |
| MMP.7 | 8619.594 | 0.595238 | 42 | 0.787879 | 33 | 75 | 0.087197 | 0.313 |
| CYFRA.21.1 | 1129.805 | 0.78125 | 32 | 0.538462 | 26 | 58 | 0.09016 | 0.356 |
| C.Peptide | 3468.038 | 0.640625 | 64 | 0.909091 | 11 | 75 | 0.093476 | 0.27 |
| CEA | 24090.46 | 0.725806 | 62 | 0.461538 | 13 | 75 | 0.099668 | 0.212 |
| sIL.1RII | 7636.054 | 0.6875 | 48 | 0.416667 | 12 | 60 | 0.102237 | 0.289 |
| sVEGFR1 | 112.065 | 0.416667 | 12 | 0.6875 | 48 | 60 | 0.102237 | 0.421 |
| HGF | 594.8866 | 0.74026 | 77 | 0.5 | 14 | 91 | 0.108812 | 0.452 |
| OPN | 41149.3 | 0.738095 | 42 | 0.5 | 16 | 58 | 0.118998 | 0.34 |
| FP | 1001.211 | 0.738095 | 42 | 0.5 | 16 | 58 | 0.118998 | 0.451 |
| IGFBP.7 | 88.26316 | 0.725806 | 62 | 0.5 | 14 | 76 | 0.119713 | 0.423 |
| MMP.2 | 29712.45 | 0.555556 | 27 | 0.75 | 48 | 75 | 0.121477 | 0.46 |
| Beta.HCG | 0.227662 | 0.866667 | 15 | 0.633333 | 60 | 75 | 0.122652 | 0.372 |
| EGF.1 | 214.3822 | 0.590909 | 22 | 0.806452 | 31 | 53 | 0.123603 | 0.319 |
| HB.EGF | 566.2644 | 0.746835 | 79 | 0.5 | 10 | 89 | 0.135974 | 0.491 |
| CA125 | 27.12589 | 0.74359 | 39 | 0.526316 | 19 | 58 | 0.137769 | 0.297 |
| EGF | 7.196994 | 0.578947 | 19 | 0.772727 | 44 | 63 | 0.138297 | 0.407 |
| Leptin.1 | 24785.75 | 0.625 | 48 | 0.9 | 10 | 58 | 0.142086 | 0.412 |
| sgp130 | 247102.2 | 0.68 | 50 | 0.4 | 10 | 60 | 0.149211 | 0.483 |
| SCF | 44.52682 | 0.833333 | 18 | 0.631579 | 57 | 75 | 0.15047 | 0.568 |
| BMP.9 | 175.4831 | 0.641026 | 39 | 0.833333 | 24 | 63 | 0.151565 | 0.529 |
| Leptin | 25030.11 | 0.666667 | 51 | 0.916667 | 12 | 63 | 0.153203 | 0.471 |
| MMP.9 | 60960.72 | 0.9 | 10 | 0.646154 | 65 | 75 | 0.153985 | 0.527 |
| MMP.1 | 1716.111 | 0.454545 | 11 | 0.71875 | 64 | 75 | 0.158025 | 0.535 |
| TNF.Alpha | 60.611 | 0.71875 | 64 | 0.454545 | 11 | 75 | 0.158025 | 0.471 |
| G.CSF | 29.014 | 0.76 | 50 | 0.538462 | 13 | 63 | 0.167521 | 0.572 |
| TRAIL | 43.58466 | 0.809524 | 21 | 0.62963 | 54 | 75 | 0.173113 | 0.63 |
| IGFBP.2 | 4.596466 | 0.5 | 12 | 0.71875 | 64 | 76 | 0.178147 | 0.6 |
| sIL.4R | 2621.552 | 0.724138 | 29 | 0.548387 | 31 | 60 | 0.188122 | 0.579 |
| IGFBP.6 | 93.69005 | 0.576923 | 26 | 0.74 | 50 | 76 | 0.194708 | 0.64 |
| PDGF.AB.BB | 53802.61 | 0.756757 | 37 | 0.605263 | 38 | 75 | 0.2169 | 0.759 |
| Epiregulin | 27.317 | 0.793103 | 29 | 0.625 | 24 | 53 | 0.226799 | 0.655 |
| sVEGFR2 | 15112.92 | 0.682927 | 41 | 0.526316 | 19 | 60 | 0.263893 | 0.675 |
| FGF.1 | 22.43221 | 0.74359 | 78 | 0.545455 | 11 | 89 | 0.27982 | 0.558 |
| HE4 | 2394.042 | 0.738095 | 42 | 0.606061 | 33 | 75 | 0.318789 | 0.847 |
| IGFBP.1 | 4.214632 | 0.742857 | 35 | 0.634146 | 41 | 76 | 0.33443 | 0.836 |
| TGF.alpha | 25.20851 | 0.655172 | 58 | 0.777778 | 18 | 76 | 0.396001 | 0.889 |
| IL.8 | 8.220301 | 0.6 | 20 | 0.714286 | 56 | 76 | 0.405188 | 0.812 |
| FGF.2 | 43.838 | 0.735849 | 53 | 0.6 | 10 | 63 | 0.452219 | 0.778 |
| PLGF | 19.93105 | 0.75 | 56 | 0.666667 | 33 | 89 | 0.466906 | 0.959 |

TABLE IV

Post Treatment Cohort

| Biomarker | Cutoff | Prop. ≤ cutoff | No. ≤ Cutoff | Prop. > Cutoff | No > Cutoff | Total No. | Optimal p-value | Adjusted p-value |
|---|---|---|---|---|---|---|---|---|
| TRAIL | 60.26394 | 0.485714 | 35 | 0.828947 | 76 | 111 | 0.00046 | 0.003 |
| sTNFRI | 1506.637 | 0.83871 | 62 | 0.5 | 34 | 96 | 0.000738 | 0.005 |
| IGFBP.1 | 9.170897 | 0.795455 | 88 | 0.409091 | 22 | 110 | 0.000918 | 0.005 |
| sEGFR | 50565.21 | 0.5 | 36 | 0.823529 | 68 | 104 | 0.001168 | 0.007 |
| IGF.1 | 7807.722 | 0.5 | 32 | 0.807692 | 78 | 110 | 0.002077 | 0.008 |
| TGF.beta1 | 9073.747 | 0.3 | 10 | 0.792208 | 77 | 87 | 0.002814 | 0.016 |
| HGF | 239.72 | 0.802469 | 81 | 0.5 | 30 | 111 | 0.003543 | 0.034 |
| MMP.7 | 8326.919 | 0.823529 | 68 | 0.55814 | 43 | 111 | 0.004292 | 0.024 |
| MMP.2 | 33782.48 | 0.516129 | 31 | 0.8 | 80 | 111 | 0.004435 | 0.027 |
| FP | 964.1461 | 0.650794 | 63 | 0.9 | 40 | 103 | 0.005027 | 0.031 |
| OPN | 34067.17 | 0.877551 | 49 | 0.62963 | 54 | 103 | 0.005844 | 0.034 |
| sVEGFR2 | 10846.5 | 0.384615 | 13 | 0.771084 | 83 | 96 | 0.007303 | 0.049 |
| IL.6 | 8.036509 | 0.833333 | 66 | 0.594595 | 37 | 103 | 0.009841 | 0.035 |
| CYFRA.21.1 | 768.7162 | 0.862745 | 51 | 0.634615 | 52 | 103 | 0.01185 | 0.03 |
| IGF.II | 507.7223 | 0.540541 | 37 | 0.794118 | 68 | 105 | 0.01287 | 0.083 |
| sTNFRII | 7588.941 | 0.8 | 65 | 0.548387 | 31 | 96 | 0.015052 | 0.093 |
| CA.15.3 | 34.52987 | 0.783133 | 83 | 0.535714 | 28 | 111 | 0.015644 | 0.056 |
| sCD30 | 129.7465 | 0.657534 | 73 | 0.913043 | 23 | 96 | 0.017669 | 0.081 |
| sIL.4R | 2096.678 | 0.428571 | 14 | 0.768293 | 82 | 96 | 0.020119 | 0.103 |
| sIL.2Ralpha | 836.577 | 0.818182 | 55 | 0.585366 | 41 | 96 | 0.020477 | 0.118 |
| IGFBP.7 | 53.66313 | 0.944444 | 18 | 0.673913 | 92 | 110 | 0.021058 | 0.137 |
| TNF.Alpha | 91.0655 | 0.666667 | 93 | 0.941176 | 17 | 110 | 0.021294 | 0.114 |
| VEGF | 1297.73 | 0.755102 | 98 | 0.428571 | 14 | 112 | 0.022711 | 0.05 |
| Follistatin | 968.871 | 0.363636 | 11 | 0.9 | 10 | 21 | 0.023736 | 0.013 |
| Leptin.1 | 11840.03 | 0.654545 | 55 | 0.854167 | 48 | 103 | 0.023887 | 0.154 |
| IGFBP.3 | 1486.814 | 0.766667 | 90 | 0.5 | 20 | 110 | 0.026339 | 0.161 |
| PLGF | 86.76473 | 0.710145 | 69 | 0.3 | 10 | 79 | 0.026822 | 0.127 |
| IGFBP.5 | 193.509 | 0.840909 | 44 | 0.636364 | 66 | 110 | 0.029601 | 0.166 |
| GRO | 4254.61 | 0.65 | 80 | 0.866667 | 30 | 110 | 0.033305 | 0.162 |
| IL.8 | 63.90276 | 0.75 | 96 | 0.466667 | 15 | 111 | 0.033355 | 0.178 |
| HE4 | 2993.413 | 0.772727 | 88 | 0.521739 | 23 | 111 | 0.034259 | 0.201 |
| IGFBP.2 | 22.89657 | 0.796875 | 64 | 0.608696 | 46 | 110 | 0.034418 | 0.169 |
| PDGF.AA | 10851.41 | 0.416667 | 12 | 0.744898 | 98 | 110 | 0.03748 | 0.218 |
| Beta.HCG | 0.1585 | 0.884615 | 26 | 0.670588 | 85 | 111 | 0.044598 | 0.239 |
| RANTES | 112016.4 | 0.677083 | 96 | 0.928571 | 14 | 110 | 0.062467 | 0.353 |
| Amphiregulin | 18.45182 | 0.818182 | 22 | 0.588235 | 51 | 73 | 0.066034 | 0.236 |
| FGF.2.1 | 66.75736 | 0.677966 | 59 | 0.840909 | 44 | 103 | 0.069765 | 0.338 |
| sgp130 | 242843.7 | 0.771429 | 70 | 0.576923 | 26 | 96 | 0.075576 | 0.348 |
| C.Peptide | 3348.411 | 0.734694 | 98 | 0.454545 | 11 | 109 | 0.078178 | 0.289 |
| CA.19.9 | 9.618456 | 0.615385 | 39 | 0.777778 | 72 | 111 | 0.079573 | 0.34 |
| Endoglin | 662.959 | 0.4 | 10 | 0.818182 | 11 | 21 | 0.080495 | 0.042 |
| Total.PSA | 528.9822 | 0.764706 | 85 | 0.576923 | 26 | 111 | 0.080808 | 0.25 |
| Tenascin.C | 3835.28 | 0.698413 | 63 | 0.4 | 10 | 73 | 0.081497 | 0.309 |
| PDGF.AB.BB | 66331.14 | 0.673913 | 92 | 0.888889 | 18 | 110 | 0.089174 | 0.436 |
| sVEGFR1 | 360.3484 | 0.763158 | 76 | 0.55 | 20 | 96 | 0.091301 | 0.412 |
| TGF.alpha | 9.548921 | 0.783333 | 60 | 0.634615 | 52 | 112 | 0.096262 | 0.408 |
| HB.EGF | 311.0071 | 0.542857 | 35 | 0.733333 | 45 | 80 | 0.099623 | 0.442 |
| sVEGFR3 | 2158.519 | 0.66129 | 62 | 0.823529 | 34 | 96 | 0.102868 | 0.428 |
| IGFBP.4 | 79.29117 | 0.752809 | 89 | 0.571429 | 21 | 110 | 0.111044 | 0.546 |
| MMP.1 | 6532.742 | 0.766234 | 77 | 0.617647 | 34 | 111 | 0.115508 | 0.467 |
| sIL.1RI | 65.47095 | 0.753086 | 81 | 0.533333 | 15 | 96 | 0.116428 | 0.506 |
| CA125 | 56.64133 | 0.777778 | 81 | 0.636364 | 22 | 103 | 0.180181 | 0.453 |
| MIF | 303.2853 | 0.671875 | 64 | 0.787234 | 47 | 111 | 0.204763 | 0.685 |
| MMP.9 | 55018.82 | 0.833333 | 24 | 0.689655 | 87 | 111 | 0.204937 | 0.752 |
| FGF.1 | 10.48625 | 0.6 | 50 | 0.758621 | 29 | 79 | 0.218824 | 0.596 |
| SCF | 77.97 | 0.741935 | 93 | 0.611111 | 18 | 111 | 0.264052 | 0.827 |
| sIL.1RII | 9586.476 | 0.697674 | 86 | 0.9 | 10 | 96 | 0.273533 | 0.817 |
| PDGF.BB | 28385.66 | 0.68254 | 63 | 0.5 | 10 | 73 | 0.295399 | 0.791 |
| Betacellulin | 17.683 | 0.717949 | 39 | 0.588235 | 34 | 73 | 0.323903 | 0.877 |
| Prolactin | 15306.05 | 0.764045 | 89 | 0.642857 | 14 | 103 | 0.335635 | 0.848 |
| EGF.1 | 31.14602 | 0.785714 | 14 | 0.627119 | 59 | 73 | 0.354469 | 0.865 |
| sIL.6R | 16360.28 | 0.683333 | 60 | 0.777778 | 36 | 96 | 0.357432 | 0.938 |
| MMP.10 | 290.6754 | 0.75 | 72 | 0.666667 | 39 | 111 | 0.380985 | 0.877 |
| G.CSF | 4.271 | 0.727273 | 11 | 0.5 | 10 | 21 | 0.386997 | 0.252 |
| BMP.9 | 167.918 | 0.5 | 10 | 0.727273 | 11 | 21 | 0.386997 | 0.228 |
| Leptin | 10637.02 | 0.5 | 10 | 0.727273 | 11 | 21 | 0.386997 | 0.236 |
| VEGF.C | 75.486 | 0.5 | 10 | 0.727273 | 11 | 21 | 0.386997 | 0.225 |
| VEGF.A | 228.021 | 0.727273 | 11 | 0.5 | 10 | 21 | 0.386997 | 0.232 |
| CEA | 24257.18 | 0.702128 | 94 | 0.823529 | 17 | 111 | 0.388648 | 0.739 |
| TNF.alpha | 2.975929 | 0.666667 | 21 | 0.768293 | 82 | 103 | 0.400402 | 0.966 |
| SRAGE | 54.18307 | 0.8 | 20 | 0.697368 | 76 | 96 | 0.417848 | 0.922 |
| Epiregulin | 71.12777 | 0.678571 | 56 | 0.588235 | 17 | 73 | 0.564203 | 0.636 |
| IGFBP.6 | 150.9202 | 0.704545 | 88 | 0.772727 | 22 | 110 | 0.605457 | 1.00 |
| EGF | 5.662 | 0.7 | 10 | 0.545455 | 11 | 21 | 0.659443 | 0.542 |
| Angiopoietin.2 | 1761.646 | 0.545455 | 11 | 0.7 | 10 | 21 | 0.659443 | 0.524 |

TABLE IV-continued

Post Treatment Cohort

| Biomarker | Cutoff | Prop. ≤ cutoff | No. ≤ Cutoff | Prop. > Cutoff | No > Cutoff | Total No. | Optimal p-value | Adjusted p-value |
|---|---|---|---|---|---|---|---|---|
| Endothelin.1 | 3.598 | 0.7 | 10 | 0.545455 | 11 | 21 | 0.659443 | 0.392 |
| VEGF.D | 49.626 | 0.545455 | 11 | 0.7 | 10 | 21 | 0.659443 | 0.571 |

The practice of the present invention will employ, unless otherwise indicated, conventional methods for measuring the level of the biomarker within the skill of the art. The techniques may include, but are not limited to, molecular biology and immunology. Such techniques are explained fully in the literature. See, e.g., Sambrook, et al. Molecular Cloning: A Laboratory Manual (Current Edition, Cold Spring Harbor Laboratory Press, Cold Spring Harbor, N.Y.); Current Protocols in Molecular Biology (Eds. A Ausubel et al., NY: John Wiley & Sons, Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition).

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. ACS. American Cancer Society. Cancer Facts & FIGS. 2013. 2013 [cited 2013 Jun. 6, 2013]; Available from: http://www.cancer.orq/acs/groups/content/@epidemiologysurveilance/documents/document/acspc-036845.pdf
2. Jemal A, Center M M, Ward E, Thun M J. Cancer occurrence. Methods Mol Biol 2009; 471: 3-29.
3. Jemal A, Thun M J, Ries L A, et al. Annual report to the nation on the status of cancer, 1975-2005, featuring trends in lung cancer, tobacco use, and tobacco control. J Natl Cancer Inst 2008; 100: 1672-94.
4. Fidias P M, Dakhil S R, Lyss A P, et al. Phase III study of immediate compared with delayed docetaxel after front-line therapy with gemcitabine plus carboplatin in advanced non-small-cell lung cancer. J Clin Oncol 2009; 27: 591-8.
5. Goldstraw P, Crowley J, Chansky K, et al. The IASLC Lung Cancer Staging Project: proposals for the revision of the TNM stage groupings in the forthcoming (seventh) edition of the TNM Classification of malignant tumours. J Thorac Oncol 2007; 2: 706-14.
6. Groome P A, Bolejack V, Crowley J J, et al. The IASLC Lung Cancer Staging Project: validation of the proposals for revision of the T, N, and M descriptors and consequent stage groupings in the forthcoming (seventh) edition of the TNM classification of malignant tumours. J Thorac Oncol 2007; 2: 694-705.
7. Borgia J A, Basu S, Faber L P, et al. Establishment of a multi-analyte serum biomarker panel to identify lymph node metastases in non-small cell lung cancer. J Thorac Oncol 2009; 4: 338-47.
8. Farlow E C, Patel K, Basu S, et al. Development of a multiplexed tumor-associated autoantibody-based blood test for the detection of non-small cell lung cancer. Clin Cancer Res 2010; 16: 3452-62.
9. Patel K, Farlow E C, Kim A W, et al. Enhancement of a multianalyte serum biomarker panel to identify lymph node metastases in non-small cell lung cancer with circulating autoantibody biomarkers. Int J Cancer 2010; 129: 133-42.
10. Shersher D D, Vercillo M S, Fhied C, et al. Biomarkers of the Insulin-Like Growth Factor Pathway Predict Progression and Outcome in Lung Cancer. Ann Thorac Surg 2011.
11. Borgia J A, Basu S, Faber L P, et al. Establishment of a multi-analyte serum biomarker panel to identify lymph node metastases in non-small cell lung cancer. J Thorac Oncol 2009; 4: 338-47.
12. R Core Team (2013). R: A language and environment for statistical computing. R Foundation for Statistical Computing, Vienna, Austria URL http://www.R-project.orq/

The invention claimed is:

1. A method for measuring a panel of biomarkers in a subject suspected of having rapidly progressing lung cancer the method comprising:
    obtaining a biological sample from the subject;
    determining whether the subject is treatment naïve or has received at least one treatment;
    assaying a level of each biomarker in a first biomarker panel or a second biomarker panel in the biological sample, the first biomarker panel comprising sTNFRI, sTNFRII, CA 19-9, Follistatin, Total PSA, TNF-α and IL-6 for treatment naïve subjects and the second biomarker panel comprising TRAIL, sTNFRI, IGFBP-1, sEGFR, IGF-1, TGF-β, HGF, MMP-7, MMP-2, α-fetoprotein, Osteopontin, sVEGFR2 and IL-6 for subjects having received at least one treatment.

2. The method according to claim 1, comprising determining the level of each biomarker for the first panel of biomarkers wherein the first biomarker-panel consists of sTNFRI, sTNFRII, CA 19-9, Follistatin, Total PSA, TNF-α and IL-6.

3. The method according to claim 1, comprising determining the level of each biomarker for the second panel of biomarkers wherein the second biomarker panel consists of TRAIL, sTNFRI, IGFBP-1, sEGFR, IGF-1, TGF-β, HGF, MMP-7, MMP-2, α-fetoprotein, Osteopontin, sVEGFR2 and IL 6.

4. The method according to claim 1, wherein the lung cancer is non-small cell lung cancer.

5. The method according to claim 1, wherein the biological sample comprises plasma sample or serum sample.

* * * * *